United States Patent [19]

Papir

[11] Patent Number: 4,579,679
[45] Date of Patent: * Apr. 1, 1986

[54] ELECTROACTIVE POLYMERS

[75] Inventor: Yoram S. Papir, Concord, Calif.

[73] Assignee: Chevron Research Company, San Francisco, Calif.

[*] Notice: The portion of the term of this patent subsequent to May 28, 2002 has been disclaimed.

[21] Appl. No.: 700,238

[22] Filed: Feb. 11, 1985

Related U.S. Application Data

[63] Continuation-in-part of Ser. No. 442,531, Nov. 17, 1982, Pat. No. 4,519,938, and a continuation-in-part of Ser. No. 370,231, Apr. 22, 1982, Pat. No. 4,519,937, said Ser. No. 370,231, is a continuation-in-part of Ser. No. 304,410, Sep. 21, 1981, abandoned, which is a continuation-in-part of Ser. No. 264,915, May 18, 1981, abandoned.

[51] Int. Cl.$^4$ .............................................. H01B 1/00
[52] U.S. Cl. ................................... 252/500; 252/510; 252/512; 252/514; 252/518; 528/183; 528/210; 528/342; 528/363; 528/374
[58] Field of Search ............... 252/500, 510, 512, 518, 252/514; 528/183, 210, 342, 363, 374

[56] References Cited

U.S. PATENT DOCUMENTS

| | | | |
|---|---|---|---|
| 3,536,781 | 10/1970 | Cotter et al. | 260/860 |
| 3,691,105 | 9/1972 | Juna et al. | 252/519 |
| 3,828,008 | 8/1975 | Shinohara et al. | 260/78.4 N |
| 3,966,987 | 6/1976 | Suzuki et al. | 252/500 |
| 4,156,757 | 5/1979 | Graser et al. | 428/411 |
| 4,222,903 | 9/1980 | Heeger et al. | 252/518 |
| 4,230,604 | 10/1980 | Wingrave | 252/518 |
| 4,338,222 | 7/1982 | Limberg et al. | 252/500 |
| 4,344,869 | 8/1982 | Blinne et al. | 252/517 |
| 4,344,870 | 8/1982 | Blinne et al. | 252/517 |
| 4,375,427 | 3/1983 | Miller et al. | 252/512 |
| 4,452,725 | 6/1984 | Wellinghoff et al. | 252/500 |
| 4,502,980 | 3/1985 | Denisevich, Jr. et al. | 252/500 |
| 4,505,840 | 3/1985 | Kurkov | 252/500 |
| 4,505,841 | 3/1985 | Denisevich, Jr. | 252/500 |
| 4,505,842 | 3/1985 | Kurkov et al. | 252/500 |
| 4,505,843 | 3/1985 | Suzuki et al. | 252/500 |
| 4,505,844 | 3/1985 | Denisevich, Jr. | 252/500 |
| 4,519,937 | 5/1985 | Papir | 252/500 |
| 4,519,938 | 5/1985 | Papir | 252/500 |
| 4,519,940 | 5/1985 | Schroeder et al. | 252/500 |
| 4,522,745 | 6/1985 | Kurkov | 252/500 |

FOREIGN PATENT DOCUMENTS

| | | | |
|---|---|---|---|
| 0054587 | 6/1982 | European Pat. Off. | 252/500 |
| 7030108 | 9/1970 | Japan | 252/500 |
| 57-034605 | 2/1982 | Japan . | |

OTHER PUBLICATIONS

"Anodic Oxidation Pathways of Carbazoles" by J. F. Ambrose & R. F. Nelson (pp. 1159–1164) 1968, J. Elec. Soc., vol. 115, No. 11.

*Primary Examiner*—Lester L. Lee
*Attorney, Agent, or Firm*—S. R La Paglia; E. J. Keeling; A. S. Zavell

[57] ABSTRACT

Tractable doped electroactive polymers, comprising recurring units of a fused nitrogen-containing unsaturated heterocyclic ring system, are fabricated from the virgin polymer by contacting the polymer with donor or acceptor conductivity modifier atoms or groups of atoms.

35 Claims, No Drawings

ELECTROACTIVE POLYMERS

CROSS-REFERENCE TO RELATED APPLICATIONS

This is a continuation-in-part application of application Ser. No. 442,531 filed Nov. 17, 1982 now U.S. Pat. No. 4,519,938, and Ser. No. 370,231 filed Apr. 22, 1982 now U.S. Pat. No. 4,519,937, wherein application Ser. No. 370,231 is a continuation-in-part of Ser. No. 304,410, filed Sept. 21, 1981, now abandoned, which is a continuation-in-part application of application Ser. No. 264,915, filed May 18, 1981 now abandoned, all of said applications incorporated herein by reference for all purposes.

BACKGROUND OF THE INVENTION

This invention relates to electroactive organic polymeric materials. More specifically, this invention relates to incorporating electroactivating agents known in the art as dopants.

Recently, research has been conducted into organic polymeric materials in order to modify their room temperature electrical conductivity by reacting them with electron donor or acceptor molecules. The electron donor or acceptor molecules, generally known in the art as n- and p-type dopants respectively, can transform the organic polymeric materials so that these modified organic polymeric materials exhibit semiconducting and metallic room temperature electrical conductivity. Polyacetylene is an example of an organic polymeric material whose room temperature electrical conductivity can be modified over several orders of magnitude above its insulator state, by the incorporation of dopant molecules, A. J. Heeger et al, U.S. Pat. No. 4,222,903, said patent incorporated herein by reference. Other examples of organic polymeric materials whose room temperature electrical conductivity can be enhanced by several orders of magnitude over their insulator state by means of incorporation of dopant molecules are poly-p-phenylene, polypyrrole, poly-1,6 heptadiyne, and polyphenylene vinylene. However, all of the above recited examples are of organic polymeric materials which are completely insoluble or infusable and hence are completely intractable.

Other examples of organic polymers whose room temperature electrical conductivity can be modified with the aid of dopants are polyphenylene sulfide and poly-m-phenylene. However, the above recited materials though being tractable in their original virgin state, undergo irreversible chemistry when reacted with dopants which modify their room temperature electrical conductivity. This irreversible chemistry imparts upon these dopant modified organic polymeric materials a state of intractability. Upon removal of the doping agents, these materials do not revert to the chemical structure which they originally exhibited prior to being modified by the dopants. The inorganic material polysulfur nitride is also considered a polymeric conductor. As with the previously recited polymeric materials, polysulfur nitride is also completely intractable.

For use in a wide variety of electronic device applications, it is highly desirable to have available organic polymeric electrically conducting materials having a preselected room temperature conductivity which can be varied over a broad range. This range should preferably extend from the insulator state of the unmodified organic polymeric material through the semiconductor regime and extending into the highly conducting metallic state. It is also desirable that these organic polymeric electrically conducting materials should be tractable and hence processable so that useful articles of any desired shape and size can be fabricated. Tractable organic polymers are those which can be readily shaped, formed, molded, pressed, cast, etc., into desired articles from the liquid state, i.e. either from the melt, fluid glassy state, or from solution after the completion of the polymerization reaction of the organic polymeric material.

SUMMARY OF THE INVENTION

I have invented an electroactive polymeric material comprising a dopant modified organic polymer whose room temperature electrical conductivity is controlled in a highly selective and reversible manner. Electroactive polymer is defined as a polymer having a conductivity which has been modified with electron acceptor or donor dopants to be greater than the conductivity of the virgin state of the polymer. The electroactive organic polymeric material is fabricated from a virgin polymer, which in itself is completely tractable and processable and which exhibits excellent mechanical and thermal properties as well as being highly stable to oxidative degradation, by modifying the polymer with a conductivity modifier, i.e. electron donor dopants or electron acceptor dopants. The electroactive organic polymeric material is comprised of recurring units of a fused nitrogen-containing unsaturated heterocyclic ring system and a conductivity modifier. More specifically, the electroactive polymer is a charged, either positive or negative, polymer backbone incorporating charge-compensating ionic dopants, i.e. ions of opposite charge to the charge of the polymer backbone. The recurring units are diradicals. The diradicals are directly linked to one another, or may be connected to one another via connecting units. A connecting unit is defined as any atom or group of atoms which can link the hereinabove diradicals together into a polymer chain.

An n-type electroactive organic polymer is obtained by reacting the virgin polymer with reducing or electron donor dopants. Electron donor dopants induce n-type conductivity in the polymer by donating an electron to the polymer and reducing same to a polyanion and the dopant is oxidized to a cation. Similarly, a p-type electroactive organic polymer is obtained by reacting the virgin polymer with oxidizing electron acceptor dopants. Electron acceptor dopants induce p-type conductivity in the polymer by oxidizing the polymer to a polycation and the dopant is reduced to an anion. The desired value of the room temperature electrical conductivity of the dopant modified electroactive organic polymer is preselected by controlling the level of incorporation of the dopants into the virgin polymer. Alternatively, the desired value of the room temperature electrical conductivity of the dopant modified electroactive organic polymer is preselected by controlling the length of the reaction time between the virgin polymer and dopants. Furthermore, the highly selective and reversible modification of the room temperature electrical conductivity of the virgin polymer can proceed by either chemical or electrochemical means. The highly selective and reversible modification of the electrical conductivity of the dopant containing organic polymeric material together with the tractability and processability of the virgin polymer is highly desirable in that the fabrication of useful articles and devices such as primary and secondary batteries, photovoltaic devices, Schottky type devices can be accomplished. Furthermore, the materials described in this invention can be utilized as active components in such devices and articles as electrochromic displays and photolithographic processes.

DETAILED DESCRIPTION OF THE INVENTION

Electroactive organic polymers are fabricated from the modification of tractable and processable virgin polymers consisting of recurring units of fused nitrogen-containing unsaturated, heterocyclic ring system by suitable conductivity modifiers. The polymers are composed of repeating diradical units derived from fused six-member nitrogen-containing ring systems wherein each ring contains no more than three nitrogens bonded sequentially. A diradical is defined as a molecule that has two unsatisfied positions available for linking into the polymer chain. Optionally, the diradicals are separated in the polymer chain by connecting units.

The fused rings contain from one through six nitrogen atoms. However, no more than two adjacent nitrogens are allowed and the nitrogens are not allowed to occupy the ring fusion positions. Suitable examples of single nitrogen fused ring systems are any of the diradicals of quinoline and isoquinoline. Suitable examples of two-nitrogen fused ring systems are any of the diradicals of cinnoline; quinazoline; quinoxaline; 2-phenylquinoxaline; phthalazine; 1,5-naphthyridine; 1,6-naphthyridine; 1,7-naphthyridine; 1,8-naphthyridine; 2,6-naphthyridine; copyrine; and the like. Suitable examples of three-nitrogen fused ring systems are any of the diradicals of 1,2,4-benzotriazine; pyrido[3,2-d]pyrimidine; pyrido[4,3-d]pyrimidine; pyrido[3,4-d]pyrimidine; pyrido[2,3-d]pyrimidine; pyrido[2,3-b]pyrazine; pyrido[3,4-b]pyrazine; pyrido[2,3-d]pyridazine; pyrido[3,4-d]pyridazine; and the like. Suitable examples of four-nitrogen fused ring systems are any of the diradicals of pyridazino[4,5-c]pyridazine; pyrimido[5,4-d]pyrimidine; pteridine; pyrimido[4,5-d]pyridazine; pyrimido[4,5-d]pyrimidine; pyrazino[2,3-b]pyrazine; pyrazino[2,3-d]pyridazine; pyridazino[4,5-d]pyridazine; pyrimido[4,5-c]pyridazine; pyrazino[2,3-c]pyridazine; pyrido[3,2-d]-as-triazine; pyrido[2,3-e]-as-triazine; and the like. Suitable examples of five-nitrogen fused ring systems are any of the diradicals of pyrimido[4,5-e]-as-triazine; pyrimido[5,4-d]-as-triazine; and the like. Suitable examples of six-nitrogen fused ring systems are any of the diradicals of as-triazino[6,5-d]-as-triazine; and the like. All the previously mentioned fused nitrogen ring systems are known and disclosed in The Ring Index, second edition, and Supplements I, II and III, Patterson et al, American Chemical Society. The molecules are synthesized into polymers by methods known in the art such as treatment with $ZnCl_2$ or $FeCl_3$ and an alkyliodide, or by dichlorination followed by reaction with appropriately disubstituted molecules such as: disodium sulfide, disodium salt of ethylene glycol, and the like. The diradicals can be modified with substituents which modify the polymer properties such as electron donating or withdrawing groups by methods known in the art.

Suitable compounds in which the nitrogens are in the ionic form, include quinolinium, and the like for any of the above diradicals. The compounds are known and disclosed in The Ring Index and Supplements I, II and III. The undoped polymers are fabricated by methods known in the art.

For example, an electroactive polymer can be fabricated with recurring units of positional diradicals of quinoline, substituted quinoline, isoquinoline, substituted isoquinoline and mixtures thereof. The diradicals can be linked at the 2,4; 2,5; 2,6; 2,7; 2,8; 3,5; 3,6; 3,7; 3,8; 4,6; 4,7; 4,8; 5,7; 5,8; and 6,8 positions, but connections at the 2,6 and 3,6 positions in the polymer are preferred. The quinoline ring system is numbered as follows:

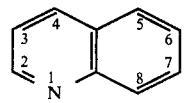

The isoquinoline ring system is numbered as follows:

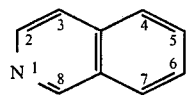

For example, the 2,6 diradical of quinoline has the formula:

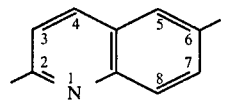

A preferred diradical of quinoline or isoquinoline is substituted in the 4-position. Preferably, the diradical is substituted with a phenyl group.

Other electroactive polymers can be fabricated with recurring units of positional diradicals of quinoxaliline, substituted derivatives thereof and mixtures thereof, and the like. The diradicals can be linked at the 2,5; 2,6; 2,7; 2,8; 3,5; 3,6; 3,7; and 3,8 positions but connections at the 2,6; 2,7; 3,6; and 3,7 positions are preferred. The quinoxaline rings system is numbered as follows:

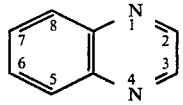

For example, the 2,6 diradical has the formula:

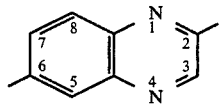

A preferred diradical of quinoxaline has a substituent in the two or three position for 3,7 or 2,6 linkages, respectively. A preferred substituent is a phenyl group.

The other nitrogen containing heterocyclic ring systems are connected in a like manner. Diradical connections through opposing portions of the fused rings are preferred as illustrative above for quinoline and quinoxaline.

The diradicals can be separated by one or more connecting units. Preferred connecting units are m-phenylene, or p-phenylene, biphenylene, —CH=CH—, and —C≡C—. The connecting units can be the same or different between adjacent diradicals in the polymer chain.

The polymer can be a homopolymer of the diradicals of quinoline, isoquinoline, quinoxaline, the previously recited diradicals and the substituted derivatives thereof or a copolymer of the diradicals. A homopolymer is defined as a polymer fabricated comprising the same recurring diradical. A copolymer is defined as a polymer comprising diradicals. In addition, the polymer is a copolymer if the same or different recurring diradicals are interspersed with connecting units.

The polymer is rendered electroactive by incorporating into the virgin polymer a conductivity modifier. More specifically, the polymer is rendered electroactive by adding electrons to (reducing) or removing electrons from (oxidizing) the virgin polymer backbone. This can be accomplished by incorporating into the virgin polymer a conductivity modifier which is either an electron donor dopant or an electron acceptor dopant. An electron donor dopant donates an electron to the polymer, the polymer becoming reduced to a polyanion and the dopant becoming oxidized to a cation. An electron acceptor dopant removes an electron from the polymer, the polymer becoming oxidized to a polycation and the dopant becoming reduced to an anion. Alternatively, the polymer can be rendered electroactive by electrochemical oxidation or reduction. In this case an electron is removed from or added to the polymer from an electrode, and charge compensating anions or cations, respectively, are incorporated into the polymer from the supporting electrolyte solution.

In both cases the resulting electroactive polymer consists of a charged polymer backbone incorporating charge-compensating ionic dopants. A suitable positively charged compensating dopant can be a cation such as the alkali metal ions, alkali earth metal ions, group III metal ions and organic cations such as

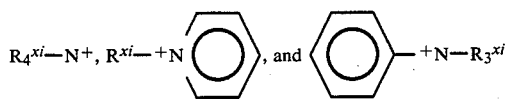

where $R^{xi}$ is a straight or branched chain alkyl of $C_1$-$C_6$ groups. Mixtures of these charge compensating dopants can be employed. These ionic dopants produce n-type conductivity when associated with a reduced or negatively charged polymer polyanion.

A suitable negatively charged compensating dopant, i.e. anionic dopants, can be an anion such as the halogen ions, other ions such as $AsF_4^-$, and preferably ions such as $AsF_6^-$, $ClO_4^-$, $PF_6^-$, $SO_3CF_3^-$, $BF_4^-$, $NO_3^-$, $POF_4^-$, $CN^-$, $SiF_5^-$, $SbCl_6$, $SbF_6^-$, $HSO_4^-$, organic anions ions such as $CH_3CO_2^-$, (acetate), $C_6H_5CO_2^-$ (benzoate), $CH_3C_6H_4SO_3^-$ (tosylate) and the like. Mixtures of the charge compensating dopants can be employed. These ionic dopants produce a p-type conductivity when associated with an oxidized or positively charged polymer polycation.

The dopant modified electroactive polymer has a charge opposite to the conductivity modifier, i.e. ionic dopant. The charges on the dopant modified electroactive polymer and the ionic dopant balance so that the dopant modified electroactive polymer is an electrically neutral system. The association of the virgin polymer with electron donor dopants produces an electroactive polymer which exhibits n-type conductivity. More specifically, reduction of the virgin polymer and the incorporation of cationic charge compensating dopants produces a polymer which exhibits n-type conductivity. The association of the virgin polymer with electron acceptor dopants produces an electroactive polymer with p-type conductivity. More specifically, oxidation of the polymer and incorporation of anionic charge compensating dopants produces a polymer with p-type conductivity.

The electroactive polymers of the invention have the following formula:

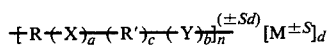

where a is either 0 or 1; b is either 0 or 1; c is either 0 or 1; n is an integer between 1 and 20,000; d is an integer between 1 and 40,000; s is an integer 1, 2, or 3; R is either an unsubstituted or substituted fused nitrogen-containing heterocyclic diradical ring system, R' is identical to or different from R; X is a connecting unit comprising of a single atom, or a group of atoms; Y is a connecting unit which is identical to or different from X; and M is an atom or a group of atoms acting as a charge compensating ion dopant whose electrical charge is opposite to the charge exhibited by the recurring repeat units:

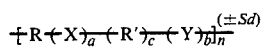

The repeat units form the polyanion or polycation of the electroactive polymer.

The diradical R group is a substituted or unsubstituted fused six-member nitrogen-containing rings. The diradicals contain from one to six nitrogens distributed between the fused six-member rings wherein each ring contains no more than 3 nitrogens bonded sequentially. Suitable R groups are the diradicals of molecules recited previously which contain from one to six nitrogens. Preferred two nitrogen fused ring systems would be composed of substituted or unsubstituted diradicals of quinoxaline.

More specifically, R and R' are unsubstituted or substituted quinolinic and isoquinolinic diradical or mixtures of diradicals which are linked to one another either directly or via the connecting units X and Y by forming bridges. Preferably the bridges are formed at the 2,6 and 3,6 positions.

The connecting units X and Y can be selected from the group comprising:

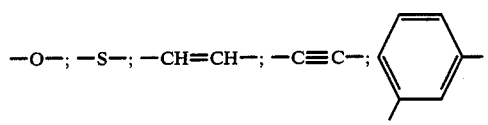

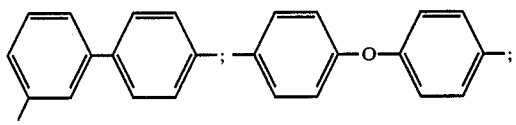

-continued

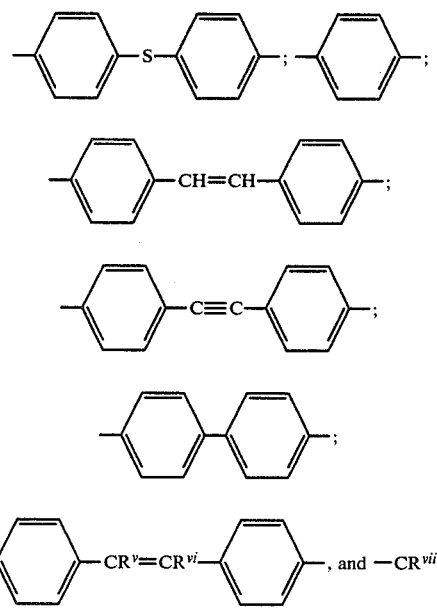

wherein $R^v$, $R^{vi}$ and $R^{vii}$ are H or methyl and mixtures thereof. Biphenyl, vinyl and acetylene connecting groups are preferred connecting units.

The size of n determines the physical properties of the electroactive polymer. Preferably, n is from 10 to 10,000 when, a, b and/or c are zero. Most preferably, n is from 50 to 5,000 when a or b are zero. Tractable films are formed with electroactive polymer whose n exceeds 50. A preferred molecular weight is 10,000 or above.

The enhancement in conductivity of the electroactive polymer above the conductivity of polymer in the virgin state is determined by d. The conductivity is increased and adjusted by increasing d. For example, the virgin homopolymer of 2,6-(4-phenylquinoline) has a conductivity of about $10^{-15}$ ohms$^{-1}$ cm$^{-1}$. Incorporating about 20 weight percent of a charge compensating ionic dopant such as Na+ in the electroactive polymer increases the conductivity to about $10^2$ ohms$^{-1}$ cm$^{-1}$. Preferred electroactive polymers are doped polymers that have conductivities greater than about $1\times10^{-10}$ ohm$^{-1}$ cm$^{-1}$, most preferably greater than $1\times10^{-4}$ ohm$^{-1}$ cm$^{-1}$. Conductivities in the range of semiconductors can be achieved when d is from about 10 to about 1000. Greater concentrations of the charge compensating ionic dopant M increase the conductivity to the metallic conductivity regime. The charge compensating cationic or anionic dopant M is selected from the previously recited dopants and the like. M remains the same for all the following preferred polymers.

The R and R' groups are the same or different. When a is 1, b and c are zero, R' and Y drop out and the polymer has the following formula:

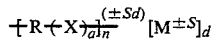

when a, b, and c are zero, $R^1$, X, Y drop out and the polymer has the formula:

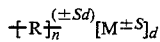

A preferred R or R' is selected from the group consisting of the diradicals of quinoline, substituted quinoline, isoquinoline, substituted isoquinoline, quinoxaline, substituted quinoxaline. A preferred diradical is a 2,6 substituted quinoline or a 2,6 substituted quinoxaline of the formula:

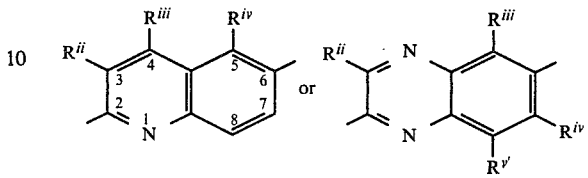

wherein $R^{ii}$, $R^{iii}$, $R^{iv}$ and $R^{v}$ are substituent groups independently selected from the group consisting of H; amino; alkyl 1 to 4 carbon atoms; alkoxy 1 to 4 carbon atoms; an alkylthio of 1 to 4 carbon atoms; a cycloaliphatic group of 5 or 6 carbon atoms; an alkenyl group of 2 to 4 carbon atoms; an aryl group of 6 to 10 carbon atoms; an aryl group of 6 to 10 carbon atoms substituted by 1 to 3 alkyl groups of 1 to 4 carbon atoms, alkenyl groups of 2 to 4 carbon atoms, alkynyl groups of 2 to 4 carbon atoms, alkoxy groups of 1 to 4 carbon atoms, 1 to 3 cyano groups, 1 to 3 halogen atoms, dialkyl amino groups of 1 to 4 carbon atoms, an alkylthiol of 1 to 4 carbon atoms; or a 5- or 6-member nitrogen containing unsaturated heterocyclic group. The nitrogen atoms in the above polymers can be quaternized by reaction with quaternizing agents, e.g. dimethyl sulfate.

The term "alkyl" refers to both straight- and branched-chain alkyl groups. Suitable examples are methyl, ethyl, propyl, isopropyl, butyl, i-butyl, s-butyl, and t-butyl.

The term "alkoxy" refers to the group $R^{10}$— wherein $R^1$ is alkyl. Suitable examples are methoxy, ethoxy, propoxy, isopropoxy, butoxy, i-butoxy, s-butoxy, and t-butoxy.

The term "alkylthio" refers to such examples as methylthio, ethylthio, propylthio, isopropylthio, butylthio, i-butylthio, t-butylthio, and s-butylthio.

Suitable examples of cycloaliphatic are cyclopentyl, cyclohexyl, 3-methylcyclopentyl, and the like.

The term "alkenyl" refers to unsaturated alkyl groups having a double bond [e.g., $CH_3CH=CH(CH_2)_2$] and includes both straight- and branched-chain alkenyl groups such as ethenyl, but-3-enyl, propenyl, and the like.

The term "aryl" refers to an aromatic hydrocarbon radical such as phenyl, naphthyl, and the like. Suitable examples of an aryl substituted with an alkyl are 2-tolyl, mesityl, 3-isopropylphenyl and the like. Suitable examples of an aryl substituted with an alkenyl are 3-styryl, 4-i-propenylphenyl, and the like. Suitable aryl groups substituted with an alkoxy are 1-methoxy-2 naphthyl, 3-n-butoxyphenyl, and the like. Suitable aryl groups substitued with a cyano group are 4-cyanophenyl, 4-cyano-1-naphthyl, and the like. Suitable examples of an aryl with a halogen are 4-fluorophenyl, 3-chloro-4-bromo-1-naphthyl, and the like. Suitable examples of an aryl substituted with a dialkyl amino are 3-dimethylaminophenyl, 6-diethylamino-2-naphthyl, and the like. Suitable examples of an aryl substituted by an alkylthio are 4-butylthiophenyl, 3-methylthio-2-naphthyl, and the like. Suitable examples of 5- or 6-member nitrogen containing heterocyclic groups are 3-pyrrolyl, 4-pyridyl, and the like.

Preferred polymers of 2,6 substituted quinoline occur when $R^{ii}$ and $R^{iv}$ are H. A preferred polymer is obtained when $R^{ii}$ and $R^{iv}$ are H and $R^{iii}$ is phenyl, i.e. poly 2,6-(4-phenylquinoline).

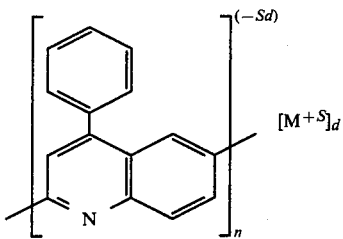

Another preferred group of polymers are obtained when $R^{iii}$ is phenyl and $R^{ii}$ and $R^{iv}$ are selected from the group of substituents previously recited.

Still another preferred polymer is fabricated from 2,6-(4-phenylquinoline) diradicals wherein a $CH_3^+$ moiety is directly linked to the nitrogen of the quinoline diradical, i.e. quaternized.

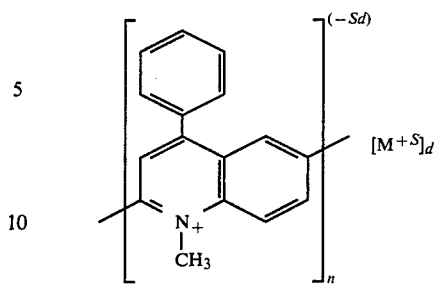

Another preferred polymer is fabricated of 2,6-(4-(4'pyridyl)quinoline) and/or its quaternized analog. When R and $R^1$ are the same and are the 2,6 quinolinic diradical unit, the recurring repeat unit of the dopant modified electroactive polymer is:

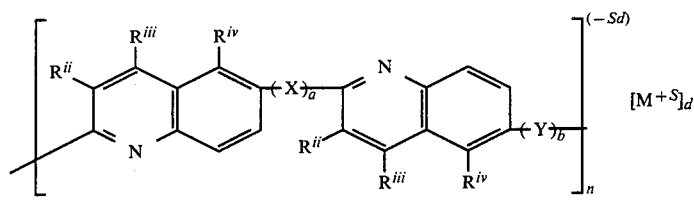

wherein $R^{ii}$, $R^{iii}$, and $R^{iv}$ are substituents selected from the groups recited above and X and Y are the connecting units previously recited. M is a previously recited conductivity modifier.

A preferred polymer has the formula

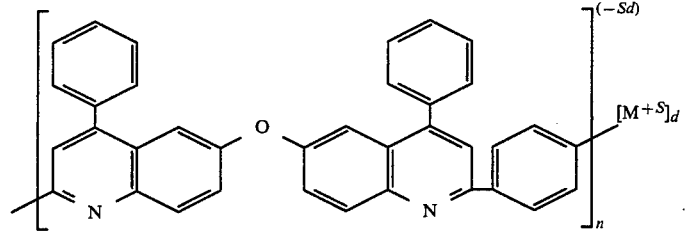

wherein $R^{ii}$ and $R^{iv}$ are H, $R^{iii}$ is phenyl a, b and C are 1, X is O and Y is a phenylene diradical.

Another preferred polymer has the formula

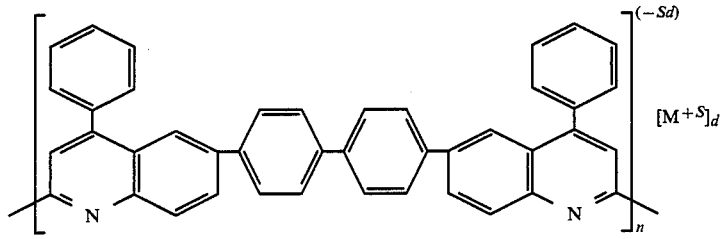

wherein $R^{ii}$ and $R^{iv}$ are H, $R^{iii}$ is phenyl, a and c are 1, b is zero, and X is a biphenylene diradical.

Another preferred polymer has the formula:

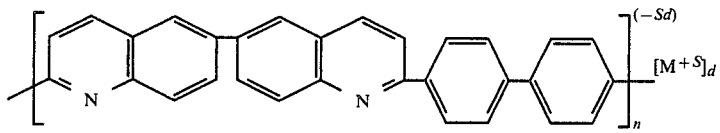

wherein $R^{ii}$, $R^{iii}$ and $R^{iv}$ are H, a is 0, b and c are 1 and Y is a biphenylene diradical.

Another preferred polymer has the formula:

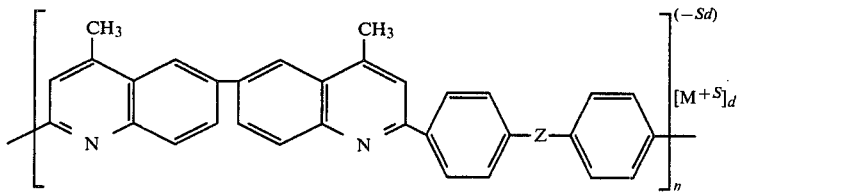

wherein $R^{ii}$ and $R^{iv}$ are H, $R^{iii}$ is —CH$_3$, a is 0, b and c are 1 and Y is

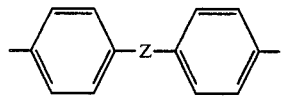

and Z is a connecting unit selected from the connecting units for X and Y or a carbon-carbon bond and then the Y unit is a biphenylene unit.

Another preferred polymer is obtained when R and $R^1$ are substituted quinoline diradicals wherein $R^{ii}$ and $R^{iv}$ are H, a is 1, b is 1, c is 1, X is —CR$^{vii}$=CR$^{vii}$— and Y is —CR$^{vii}$=CH—. The polymer has the formula:

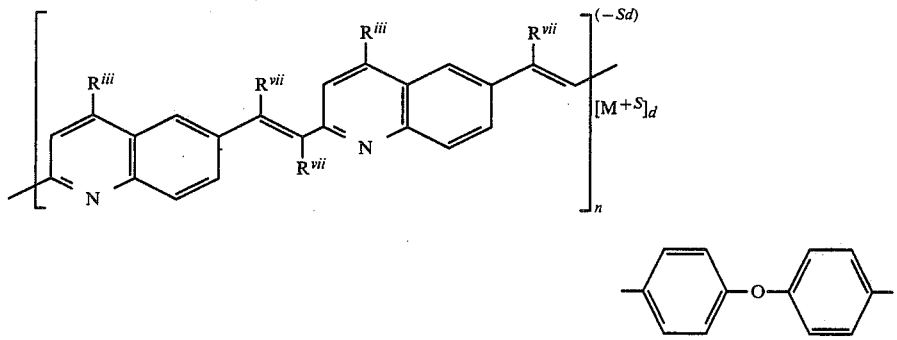

Still another preferred polymer is when $R^{iii}$ is phenyl and $R^{vii}$ is H.

When R or R' are substituted isoquinoline diradical, a preferred diradical has the formula:

wherein $R^{viii}$, $R^{ix}$, and $R^x$ are selected from the same substituent groups as $R^{ii}$, $R^{iii}$, and $R^{iv}$. Similar polymers to the previously recited preferred quinoline polymers are also preferred for isoquinoline.

A preferred electroactive poly(phenyl quinoxaline)-polymer i.e., poly 2,2'-(p,p'-oxidiphenylene)-6,6'-Bi(3-phenylquinioxaline) has the formula:

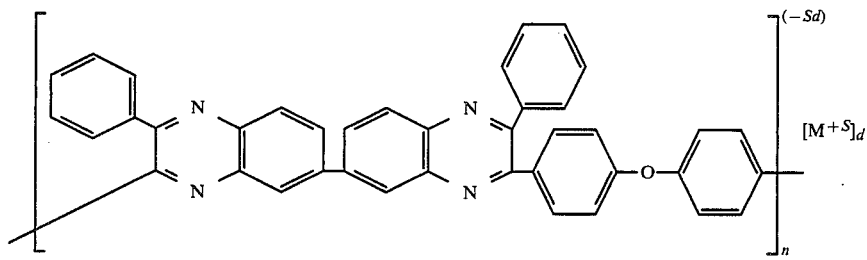

where R and R' are phenyl quinoxaline, a is 0, b and c are 1 and Y is

Another preferred quinoxaline polymer, poly 2,2'-(p-phenylene)-6,6' Bi(3-phenylquinoxaline) has the formula:

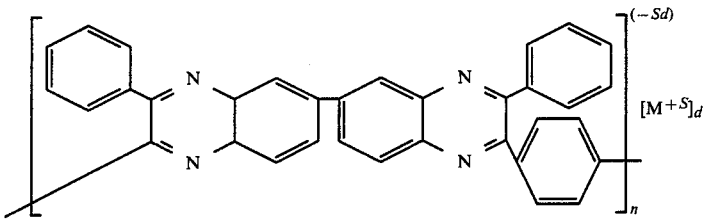

where R and R' are phenylquinoxaline, a is 0, b and c are 1 and y is p-phenylene. The virgin polymer can be made according to Hergenrother et al, J. Polym Sci., A-1, Vol 5, 1453 (1967), incorporated herein by reference.

Still another preferred quinoxaline polymer, poly 2,2'-(m-phenylene)-6,6' Bi(3-phenylquinoxaline) has the formula:

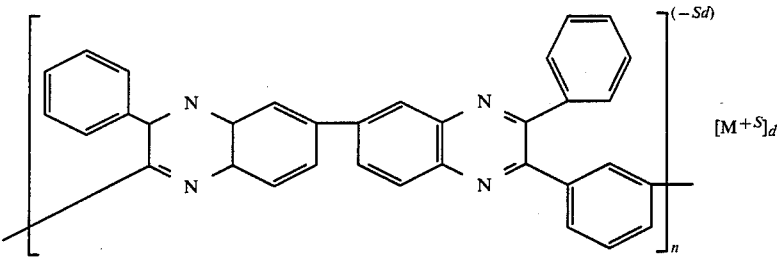

where R and R' are phenylquinoxaline, a is 0, b and c are 1, and Y is m-phenylene. The virgin polymer can be made according to the procedures in Hergenrother et al, above.

Polymer Fabrication

The starting material for preparing the electroactive polymers of this invention are polymers and copolymers comprising recurring units of fused nitrogen containing unsaturated heterocyclic ring system. Preferably the recurring units are quinoline or isoquinoline or substituted quinoline or isoquinoline. These polymers and copolymers are well known materials having been synthesized in a variety of ways. For example, quinoline, isoquinoline, or substituted derivatives thereof can be converted into polymers by treatment with zinc chloride or by treatment with $FeCl_3$ and an alkyliodide, Rabinovich et al, Dokl. Akad. Nauk SSSR 1971, 199(4), 835–7 and Smirnov et al, Vysokomol Soedin Ser B 1971, 13(6), 395–6, respectively, incorporated by reference. The method is also suitable to polymerize the other diradicals previously recited.

Other polymers are made by a synthetic route involving the reaction of the dichloro or dibromo derivatives of fused nitrogen containing unsaturated heterocyclic units with magnesium in ether followed by contacting with a nickel salt. The dihalo derivatives having halogens in essentially all possible combinations are known. This route provides a method of preparing polyquinolines or polyisoquinolines having bridges through any two of the seven possible points of attachment.

The dihalo compounds are also useful in forming copolymers with other interconnecting groups. For example reactions with sodium sulfide gives a sulfur atom between each nitrogen heterocycle. Reaction with dihydroxy or disodium salts of dihydroxy compounds give ether-type copolymers.

Another method of making the polymeric starting material is by a synthesis involving the final reaction of an appropriate diketone with an appropriate aminodiacylbenzene in the presence of a base or an acid catalyst as discussed in Korshak et al, Vysokomol, Soedin., Ser B9(3), 171–2(1967); Shopov, I, Vysokomol.Soedin., Ser B 1969, 11(4) 248; Garapon, J et al, Macromolecules 1977, 10(3) 627–32; Stille, J. K et al, Polym. Prepr., Am Chem. Soc., Div. Polym. Chem 1976, 17(1), 41–45; Stille, J. K. Pure Appl. Chem. 1978, 50(4), 273–280; Baker, G. L. et al Macromolecules 1979, 12(3), 369–73; and Beever, W. H. et al Macromolecules 1979, 12(6), 1033–8, all of said articles incorporated herein by reference.

Still another method of preparing polyquinolines useful as starting materials for the compounds of this invention is by the condensation polymerization of appropriate di(aminophenyl) compounds with appropriate di(alpha,gamma-diketo)compounds, see V. Korshak et al, Vysokomol Soedin, Ser B9(3), 171, (1967). The resulting polymers have structures of formula

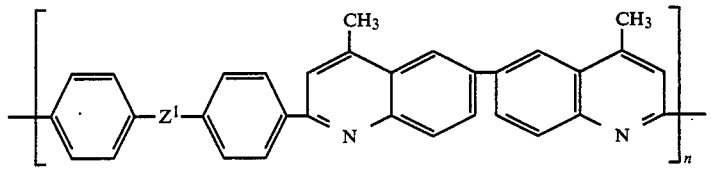

wherein $Z^1$ is O or a carbon-carbon bond.

The di(aminophenyl) compounds may contain a variety of substituents but must have an unsubstituted position ortho to the amino group. Typical compounds include 4,4'-diaminobiphenyl, 3,3'-diaminobiphenyl, 2,4'-diaminobiphenyl, 2,2'3,3'-tetramethyl-4,4'- diaminobiphenyl, di(4-aminophenyl)methane, di(4-aminophenyl)ether, 1,2-di(4-aminophenyl)ethane, 1,2-di(4-aminophenyl)ethylene, and the like.

The di(alpha,gamma-diketo) compounds comprise those compounds wherein the diketones are joined at the alpha-position through various connecting groups. These compounds have the structure:

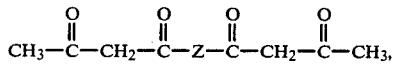

wherein Z is a connecting group. Typical connecting groups include the X and Y connecting groups having 2 or more atoms, French Pat. No. 1,468,677 and J. Polym. Sci. Part C, #16 Part 8, 4653 (1968), incorporated herein by reference.

The preferred method for making the polyquinoline polymeric starting material is in accordance with the procedures outlined by W. H. Beever, et al., Journal of Polymer Science: Polymer Symposium 65, pp. 41-53 1978; S. O. Norris, et al., Macromolecules, Vol. 9, No. 3, May-June, 1976, pp. 496-505, J. Pharm. Sci. 57 784 (1968), and J. Heterocycle Chem. 11 107 (1974), all said articles incorporated herein by reference.

Tractable Polymer Fabrication

Subsequent to polymerization, articles such as fibers, ribbons, or free-standing films are cast from solution. The solution is formed by dissolving the desired polymer in a solvent which consists of sulfuric acid, formic acid, or a mixture of $P_2O_5$ and m-cresol. The solution temperature is from about 25° C. to about 200° C. and preferably at about 140° C., most preferably 100° C. The polymers are coagulated into solid shapes such as fibers, ribbons, or free-standing films in a basic coagulation bath. For free-standing films, the polymers are fabricated from solutions containing about 2 to 25% polymer dissolved in the solvent. At concentrations which exceed 10%, the cast films take on an anisotropic morphology. The anisotropic property enhances the conductivity in the anisotropic direction. An amine, for example triethylamine, dissolved in a protonic solvent such as $H_2O$ and preferably ethyl alcohol comprises the coagulation bath. The bath is maintained at a lower temperature than the dissolution temperature of the polymer in the solvent. Usually room temperature is selected as the operating temperature of the coagulation bath. The fabricated articles are dried. Elevated temperatures, usually 60° C., and reduced pressure accelerated the drying process. Drying is continued until no further weight loss is observed.

Polymer Conductivity Modification

After fabrication of the desired articles from the polyfused heterocyclic quinolinic polymers by means of the procedure described above, the articles are rendered electroactive by, for example, chemical or electrochemical procedures. The articles can be rendered electroactive in an atmosphere which is inert with respect to the polymer and dopant, by contacting them with suitable conductivity modifiers, i.e. dopants. An inert atmosphere is defined as an atmosphere which does not react with the polymer, the dopant, or the electroactive polymer. For example, the atmosphere can be argon, helium, and nitrogen and the like. The doping can also be carried out in an inert liquid medium such as tetrahydrofuran, acetonitrile and the like. The dopants can be oxidizing or electron accepting molecules, or reducing or electron donating molecules. Both types of dopants may be in the form of gases or vapors, pure liquids or liquid solutions. Preferably, oxygen and water moisture are excluded during and after the doping process because the conductive polymers tend to degrade, i.e. lose conductivity, when exposed thereto.

For example, the polymer can be contacted with alkali naphthalides or alkali anthracenides such as sodium naphthalide, potassium naphthalide, or sodium anthracenide in a tetrahydrofuran solution. The conductivity modifier concentration can be from about 0.001 to about 1 molar and preferably from about 0.01 to about 0.5 molar in the THF or other suitable solvent. Alternative doping methods are taught in U.S. Pat. No. 4,204,216 and incorporated herein by reference.

It is unclear at the present time exactly how the electron donor or acceptor dopants are incorporated into the polymer. However, the incorporation of the dopants into the polymer can be observed by a color change in the polymer as well as an enhanced conductivity. For example, a virgin polymer film having a yellow or orange color, changes to a blue or black color with a metallic luster upon doping and the measured conductivity increases by many orders of magnitude.

Alternatively, the polyquinoline polymers can be oxidized or reduced to their conductive forms using electrochemical techniques. In this method, herein referred to as electrochemical doping, the polymer is immersed in a suitable electrolyte solution and used as one electrode of an electrochemical cell. Upon passing an electric current through such a cell the polymer becomes reduced (or oxidized, depending upon the direction of current flow) and charge compensating cations (or anions) from the supporting electrolyte become incorporated into the polymer. This doping also proceeds with the characteristic color change described above. Thus, the polymer can be electrochemically doped with whatever appropriately charged ion is present in the electrolyte solution. Electrolyte solutions are comprised of a salt dissolved in a solvent. Suitable solvents are acetonitrile, tetrahydrofuran, 2-methyl-tetrahydrofuran, propylene carbonate, dimethylformamide, dimethylsulfoxide and the like. Suitable cations are $Li^+$, $Na^+$, $K^+$, $(CH_3)_4N^+$, $(C_2H_5)_4N^+$ and $(C_4H_9)_4N^+$. Suitable anions are $Cl^-$, $Br^-$, $ClO_4^-$, $BF_4^-$, and $PF_6^-$. The extent of doping can be easily controlled by adjusting the amount of charge electrochemically injected into the polymer, either by controlling the magnitude of the current used (galvanostatic charging) or by controlling the potential of the polymer electrode with respect to a reference electrode (potentiostatic charging).

The above-described electrochemical doping process is completely reversible. The polymer can be "undoped" and returned to its original, neutral, non-conducting state simply by applying a current opposite in sign to that used for the doping process. Upon complete undoping the color of the polymer reverts back to its original color. Thus, for example, a reduced, conducting polyquinoline polymer can be reoxidized completely to its neutral, non-conducting form, and the charge-compensating cations incorporated during the electrochemical reduction process are expelled from the article during electrochemical re-oxidation.

Having described the methods of fabrication and the basic polyfused heterocyclic systems, the following examples are intended to be illustrative of the invention and not meant to limit the scope thereof. Modification which would be obvious to one of ordinary skill in the art are contemplated to be within the scope of the invention.

EXAMPLES

Example 1a

Preparation of 2-methyl-2-(4-nitrophenyl)-1,3 dioxolane

P-Nitroacetophenone (1.65 g, 10 m mol), ethylene glycol (5 ml, 89 m mol), triethyl orthoformate (2.96 g, 20 m mol), and p-toluenesulfonic acid (0.086 g, 0.5 m mol) were combined in methylene chloride (4 ml). The solution was heated with an oil bath (50°–70° C., 6 hrs), cooled to room temperature, and poured into excess 10% sodium hydroxide solution. The phases were separated and the aqueous phase was extracted twice with methylene chloride. The combined organic phase was washed three times with water and dried with anhydrous sodium sulphate. Evaporation of the solvent left a light yellow product (1.78 g) with mp. 69°–71° C., (lit. 73°–75° C., see J. Pharm. Sci. 57, 784 (1968)).

Example 1b

Preparation of 5-(2-Methyl-1,3-dioxolan-2yl)-3-phenyl-2,1-benzisoxazole

Phenylacetonitrile (0.84 g, 7.2 m mol) and 2-methyl-2-(4-nitrophenyl)-1,3-dioxolane (mp. 69°–71° C.) (1.50 g, 7.2 m mol) were added to a room temperature solution of sodium hydroxide (1.44 g, 36 m mol) in methanol (8 ml). A slight exotherm was noted and stirring was continued for 16 hrs. The mixture was filtered and the collected solid washed several times with water and once with cold methanol to yield a yellow powder (1.60 g) with mp. 137° C. (lit. mp. 137°–138° C., see J. Heterocyclic Chem. 11, 107 (1974)).

Example 1c

Preparation of 2-Amino-5-(2-methyl-1,3-dioxolan-2-yl)benzophenone 5-(2-Methyl-1,3-dioxolan-2yl)-3-phenyl-2,1-benzisoxazole (1.50 g, 5.3 m mol), triethyl amine (0.3 ml) and 5% palladium on carbon (0.15 g) were combined in dry tetrahydrofuran (13 ml). The apparatus wa flushed with nitrogen and then hydrogen. A static hydrogen atmosphere was maintained (1 atm.) and the progress of the reaction followed by gas chromatography. The starting material and product have retention times of 11.15 and 11.33 min. respectively. When conversion was complete, the mixture was filtered through a pad of Celite to yield a clear yellow solution. Evaporation of the solution yielded a yellow solid (1.35 g) of mp. 108°–111° C.

Example 1d

Preparation of 5-Acetyl-2-aminobenzophenone

2-Amino-5-(2-methyl-1,3-dioxolan-2-yl)benzophenone (1.0 g, 3.54 m mol) was dissolved in 30 ml absolute ethanol. To this was added 1M perchloric acid (14 ml). The resulting mixture was stirred at room temperature for 18 hrs. The mixture was made basic with 3N sodium hydroxide solution and then extracted with several portions of methylene chloride. The combined methylene chloride extracts were washed with water, dried with anhydrous sodium sulfate, and evaporated to yield a yellow product (0.79 g) of mp. 158°–161° C. A portion of the product was recrystallized from a mixture of methylene chloride and hexane to yield material of mp. 158°–162° C.

Example 1e

Preparation of Poly 2,6-(4-phenylquinoline)

A solution was prepared from phosphorous pentoxide (1.07 g, 7.5 m mol) and freshly distilled m-cresol (2.5 ml) by heating at 140° C. for 2.5 hrs. under nitrogen. The solution was cooled to room temperature and 5-acetyl-2-aminobenzophenone (0.30 g, 1.28 m mol) and m-cresol (1.3 ml) were added. The solution was heated to, and maintained at 120° C. for 48 hrs. The hot solution was poured with stirring into a mixture of 95% ethanol (60 ml) and triethylamine (6 ml) to yield a fibrous yellow solid which was washed twice with ethanol in a Waring blender. It was then extracted with ethanol (19 hrs) in a Soxlet apparatus and dried to give an orange product (0.26 g, 1.28 m mol).

Example 2

Preparation of Films of Poly 2,6-(4-phenylquinoline) Films

A solution was prepared from phosphorous pentoxide (0.8 g, 5.6 m mol) and distilled m-cresol (2.5 ml) by heating at 110°–120° C. under Argon. The solution was cooled to room temperature and poly 2,6-(4-phenylquinoline) (0.051 g, 0.25 m mol) added. The mixture was heated to 140° C. to yield a viscous deep red solution. Free-standing films were prepared by spreading a few drops of this solution on a heated glass plate and quenching in a bath of triethylamine (10%) and ethanol (90%). The clear yellow films were pressed between layers of filter paper and dried in a vacuum oven.

Example 3

Doping of Poly 2,6-(4-phenylquinoline)

The transparent, yellow film prepared in Example 2 was placed in a jar, in a dry box with a dry argon atmosphere. After 30 minutes, a dimethoxyethane solution of sodium naphthalide was poured into the jar. The film reacted immediately, changing to a dark color; green-blue in transmitted light and purple-green with metallic sheen in reflected light. Upon exposure to air, the dark color disappears instantly, and the polymer resumes its original appearance.

Example 4

Conductivity Measurement of Poly 2,6-(4-phenylquinoline)

The procedure of example 3 was followed except the film was first wet with tetrahydrofuran (THF) and then treated with 0.1M sodium naphthalide in THF. Upon addition of the sodium naphthalide, the polymeric film turned deep blue with a metallic luster. The surface of the film was rinsed with THF. The conductivity of the doped film ($2.54 \times 10^{-3}$ cm thick) was measured using a 4-point probe apparatus of the Signature Co. The 4 points of the apparatus form a single line. A DC voltage (VE) is applied across the outermost two points, and the voltage (VI) of the current is measured across the inner two points. From these values a conductivity is calculated as follows:

$VE = 0.1$ volts
$VI = 0.06$ volts (measured)
$R = 1074 \, (VE/VI) = 1790$ ohms/square rho = R × t = 1790 × 2.54 × 10$^{-3}$ = 4.55 ohm centimeters sigma = 1/rho = 0.22 ohm$^{-1}$ centimeter$^{-1}$ where:
VE = impressed voltage
t = film thickness
VI = measured voltage
R = resistance of the surface
rho = resistivity of the article
sigma = conductivity
1074 = instrument and unit conversion factor The washed, but undoped polymer, was not conductive, but actually was an insulator having a conductivity of 10$^{-15}$ ohms$^{-1}$ centimeter$^{-1}$ as measured on the same apparatus, (See J. Polym. Sci. Poly. Symp., 65, 41 (1978). This same value (10$^{-15}$) was measured on the doped film after turning yellow upon exposure to air.

The infrared spectra of the original undoped film and the air-exposed doped film were the same. The infrared of the dark, sodium naphthalide doped film was opaque with no absorbtion between 4000 and 600 cm$^{-1}$, indicating metallic behaviour. This experiment shows that the doped polyquinoline films are surprisingly good electrical conductors.

Example 5

Conductivity Measurement of Poly 2,6-(4-phenylquinoline)

Films were also doped as in Example 4 but with potassium naphthalide and after these films had been kept for 6 days in a vacuum dry box at a pressure less than 10$^{-6}$ mm Hg, the following conductivity value was obtained:

VE = 36 mv
VI = 55 mv
t = 2.54 × 10$^{-3}$ cm
rho = 1.78 ohm cm.
sigma = 0.56 ohm$^{-1}$ cm$^{-1}$ Values of this magnitude show the doped polymer to be electroactive in that it is a conductor of electricity.

Example 6a

Preparation of bis-4-Nitrophenylether

1-Fluoro-4-nitrobenzene (20.0 g, 0.142 mol), 4-nitrophenol (19.7 g, 0.142 mol), and potassium fluoride (28.3 g, 0.486 mol) were combined in 75 ml dimethylsulfoxide and heated to reflux for 0.5 hrs. The mixture was cooled and left at room temperature overnight.

The precipitate was collected and washed with water. It was dissolved in warm toluene, separated from a water layer and dried with magnesium sulfate. Concentration and cooling yielded 28.8 g of product (mp 144°–146° C.) in two crops.

Example 6b

Preparation of 5,5'-Oxybis-(3-phenyl-2,1-benzisoxazole)

Phenylacetonitrile (17.72 g, 0.151 mol) and bis-4-nitrophenylether (19.52 g, 0.075 mol) were added to a room temperature solution of sodium hydroxide (30.01 g, 0.75 mol) in methanol (150 ml) and heated at reflux for 9 hrs. The reaction mixture was cooled to room temperature and diluted with 50 ml of 50% methanol in water and then cooled in an ice bath. The precipitate was collected and washed with cold methanol. This solid was dissolved in warm toluene, dried with magnesium sulfate, concentrated, and cooled to yield 7.55 g. Recrystallization from warm toluene gave 5.19 g of product mp 208°–209° C. A second, unidentified material, mp 158°–165° C., was also isolated.

Example 6c

Preparation of 4,4'-Diamino-3,3'-dibenzoyldiphenylether 5,5'-Oxybis-(3-phenyl-2,1-benzisoxazole) (4.92 g, 12.0 m mol) and triethylamine (1.35 ml) were combined in tetrahydrofuran (50 ml) under a nitrogen atmosphere. Palladium on carbon (5%, 0.41 g) was added and then hydrogen was slowly passed through the system for 15 hours. The mixture was filtered through Celite and evaporated to a yellow oil which was crystallized from a mixutre of toluene and hexane (10 to 1) to yield 4.33 g (87%) of the desired product. This was further purified by recrystallization from methanol to yield 2.43 g with mp 154°–155° C.

Example 6d

Preparation of a Quinoline Copolymer from 4,4'-Diamino-3,3'-dibenzoyldiphenyl ether and p-Diacetylbenzene A solution was prepared from phosphorous pentoxide (5.6 g, 39.4 m mol) and freshly distilled m-cresol (20 ml) by heating to 140° C. A portion of this solution (7.6 ml) was used to dissolve 4,4'-diamino-3,3'-dibenzoyldiphenyl ester-(0.5005 g, 1.225 m mol) and p-diacetylbenzene (0.1987 g, 1.225 m mol). The solution was maintained at 110°–120° C. for 48 hrs. The mixture was cooled and poured into a mixture of triethylamine (10 ml) and 95% ethanol (100 ml) to yield a white fibrous product. The product was dissolved in chloroform (15 ml) and precipitated with ethanol. This was repeated to finally yield 0.10 g of white, fibrous polymer. A film was prepared by dissolving 25.7 mg in 0.52 g of the above phosphorous pentoxide-m-cresol solution at 60° C., placing a few drops on a warm glass plate, and spreading with a warm blade. After quenching in a 90% ethanol-10% triethyl amine bath, a free-standing film was obtained. This polymer has the structure:

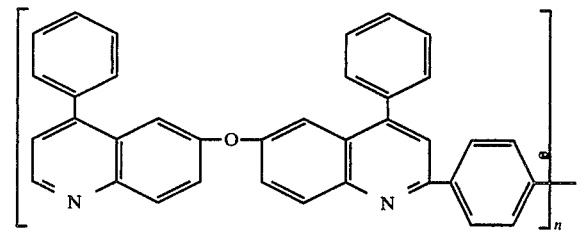

Example 7

Doping and Conductivity Measurement of the Polymer of Example 6

Films of the polymer of Example 6d were kept in a dry box for 2 weeks at less than 10 ppm water and oxygen. Thereafter the films were doped with sodium naphthalide as described in Example 3. Upon doping, the films turned a deep metallic blue in color. Conductivity measurements gave:

VE = 4.5 mV
rho = 40.92 ohm cm.
VI = 0.3 mV
sigma = 0.024 ohm$^{-1}$ cm$^{-1}$
R = 16110 ohms per square

Example 8a

Preparation of 5-Bromo-3-phenyl-2,1-benzisoxazole

Phenylacetonitrile (8.1 g, 69 m mol) was added to a room temperature solution of potassium hydroxide (85%) (74 g, 1.1 mol) in methanol (150 ml). To this was added 4-bromo-1-nitrobenzene (12.7 g, 63 m mol) suspended in methanol (130 ml). An exotherm was noted and the reaction was maintained at 50° C. for 5 hrs. After cooling to room temperature, water (400 ml) was added. The precipitate was collected and washed with water. The crude product (13.15 g) was crystallized from hot methanol (200 ml) to yield yellow needles (9.52 g, mp 113°–116° C.).

Example 8b

Preparation of 2-Amino-5-bromobenzophenone

5-Bromo-3-phenyl-2,1-benzisoxazole (7.5 g, 28.6 m mol), water (14.6 ml), and zinc dust (9.3 g, 143 m mol) were combined. Acetic acid (8.6 ml, 143 m mol) was added and the mixture was stirred and heated at 80° C. for 90 minutes. After cooling to room temperature, both the liquid and solid portion of the reaction were extracted with methylene chloride. The combined methylene chloride solutions was washed once with sodium hydroxide solution (10%) and several times with water. Drying (sodium sulfate) and evaporation yielded the desired product (7.42 g) of mp. 92°–102° C.

Example 8c

Preparation of 4,4'-Diamino-3,3'-dibenzoylbiphenyl

5-Bromo-2-aminobenzophenone (0.55 g, 2.0 m mol) was dissolved in dry and deoxygenated dimethylformamide (10 ml) in an inert atmosphere box. To this was added in portions bis(1,5-cyclooctadiene)nickel (O) (0.55 g, 2.0 m mol). The reaction was moved from the inert atmosphere box to a vacuum-argon manifold using standard Schlenk-wave techniques. The reaction was heated at 50°–55° C. for 4 hrs. and left at room temperature overnight. The mixture was poured into 200 ml of water which was made slightly basic with sodium hydroxide. The water was extracted several times with ethyl acetate which after drying with sodium sulfate and evaporation gave a dark brown liquid (0.48 g). Recrystallization from hexane yielded 100 mg of yellow brown solid mp 180°–185° C.

Example 8d

Preparation of a Polymer from 4,4'-Diamino-3,3'-dibenzoylbiphenyl and 4,4'-diacetylbiphenyl 4,4'-Diamino-3,3'-dibenzoylbiphenyl (80.0 mg, 0.204 m mol) and 4,4'-diacetylbiphenyl (48.6 mg, 0.204 mmol) were combined in a solution prepared from phosphorous pentoxide (0.348 g, 2.45 m mol) and freshly distilled m-cresol (1.2 ml) and heated at 120°–130° C. for 46 hrs. The hot reaction mixture was poured with stirring into a mixture of triethylamine (6 ml) and 95% ethanol (60 ml). The fibrous red precipitate was stirred in the basic bath until its color changed to yellow. It was washed with water and dried at 80° C. to yield 120 mg of yellow powder mp>320° C. Films of this material were prepared by dissolving 50 mg at 120° C., in m-cresol (0.75 ml) containing phosphorous pentoxide (0.2 g). A few drops of this solution were spread on a glass plate and quenched in a bath of triethylamine (10%) and ethanol (90%) to yield a free-standing yellow film. This copolymer has the structure:

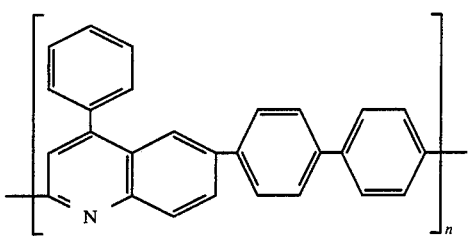

Thereafter, the polymer was rendered conductive in accordance with the procedure outlined in Example 3. The conductivity was measured in accordance with the procedures outlined in Example 4. The conductivity of the doped polymer was 0.024 ohm$^{-1}$ cm$^{-1}$.

Example 9

Preparation of Poly 2,6-(4-(4'chlorophenyl)quinoline)

This polymer was prepared by essentially the same process as described in Example 1, except that 4-chlorophenyl acetonitrile was used in place of phenylacetonitrile. Analysis of the polymer gave the following results. Calculated for ($C_{15}H_8NCl$): C, 75.80%; H, 3.39%; N, 5.89%, Cl, 14.92%. Found: C, 76.81%; H, 3.64%; N, 5.86%, the remainder being Cl. The polymer has the structure:

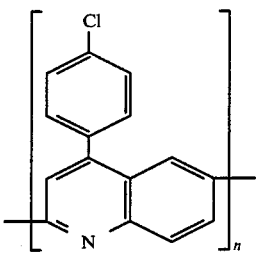

Thereafter, the polymer was rendered conductive in accordance with the procedure outlined in Example 3. The conductivity was measured in accordance with the procedures outlined in Example 4. The conductivity of the doped polymer was 0.02 ohm$^{-1}$ cm$^{-1}$.

Example 10

Electrochemically Doping Quinoline Polymers

A 5-inch platinum wire was coated with a thin film of the polymer of Example 1, by dipping the wire into a 5% solution of the polymer in a m-cresol/$P_2O_5$ mixture. The film-coated wire was neutralized by dipping into a 10% triethylamine-90% ethanol solution and dried in a vacuum oven at 60° C.

The polymer coated wire was connected to an E.G. and G. Princeton Applied Research Apparatus comprising a Universal programmer and a Potentiostat/Galvanostat, with recorder. The polymer coated end of the wire was then immersed into a 0.1M solution of lithium tetrafluoroborate in acetonitrile. A potential, varying from 0 to −3.0 volts vs. SCE was applied to the platinum wire. The output current was essentially nil until the potential reached about −1.5 volts at that point the cathodic current increased rapidly and peaked at −2.25 volts. Upon reversal of the potential sweep, an anodic current was observed which peeked at −1.5 volts. When the initial −1.5 volt potential was applied, the polymer adhering to the wire turned from a pale yellow to a dark metallic color, which color disappeared upon raising the voltage to more than −1.5 volts.

This behavior indicates an initial resistance to passage of current followed by a rapid uptake of electrons resulting in a charged electroactive polymer containing lithium ions as the charge compensating dopant. In effect the polymer was made electroactive by the application of a potential of about −2 volts in the presence of an electrolyte solution capable of providing a charge compensating dopant.

Example 11

Electrochemically Doping Quinoline Polymers

The same experiment as Example 10 was carried out except that the lithium tetrafluoroborate was replaced by tetrabutyl ammonium bromide. Essentially the same results were obtained as in Example 10. In this case the polymer coated wire was alternately charged and discharged without any loss in activity. The metallic color came and went as the polymer was charged and discharged.

This experiment indicates that the charged electroactive polymer can be used as an electron source. One useful application is as the anode of a battery. It also shows that the electroactive polymer is able to incorporate into its structure organic charge compensating ionic dopants.

Example 12

Electrochemically Doping of a Poly(phenyl-quinoxaline)

A 5-inch platinum wire was coated with a thin film of a polymer of the structure by dipping the wire into a 5% solution of the polymer in an m-cresol/P$_2$O$_5$ mixture. The virgin polymer was purchased through the Aldrich Chemical Co. and is a product of Scientific Polymer Product, Inc., 6265 Dean Parkway, Ontario, N.Y. Catalogue #330 lot 101. The polymer is 100% solids in m-cresol. The film-coated wire was neutralized by dipping into a 10% triethylamine-90% ethanol solution and dried in a vacuum oven at 60° C.

The polymer coated wire was connected to an E.G and G. Princeton Applied Research Apparatus comprising a Universal programmer and a Potentiostat/-Galvanostat, with recorder. The polymer coated end of the wire was then immersed into a 0.1M solution of lithium tetrafluoroborate in acetonitrile. A potential, varying from 0 to −3.0 volts vs. SCE was applied to the platinum wire. The output current was essentially nil until the potential reached about −1.5 volts. At that point the cathodic current increased rapidly and peaked at −2.0 volts. Upon reversal of the potential sweep, an anodic current was observed which peaked at −1.25 volts. When the initial −1.5 volt potential was applied, the polymer adhering to the wire turned from a pale yellow to a dark metallic color, which color disappeared upon raising the voltage to more than −1.5 volts.

This behavior indicates an initial resistance to passage of current followed by a rapid uptake of electrons resulting in a charged polymer containing lithium ions as the charge compensating dopant. In effect the polymer was made electroactive by the application of a potential of about −2 volts in the presence of an electrolyte capable of providing charge compensating ionic dopants.

Example 13a

Preparation of 4-Acetyl-2-(4$^1$-methoxy)benzoyl Aniline Monomer 38.2 g of NaOH was dissolved in metanol (200 ml) in a 1-liter 3-neck flask provided with a mechanical stirrer, reflux condenser, N$_2$ inlet and a heating mantle. 28.14 g (0.19 mol) of p-methoxyphenyl-acetonitrile was added followed by 40 g (0.191 moles) of p-nitro-acetophenone ethylene glycol ketal. The reaction was stirred mechanically under reflux for 22 hours.

The product was filtered off, washed with water and recrystallized from methanol.

The product had the formula:

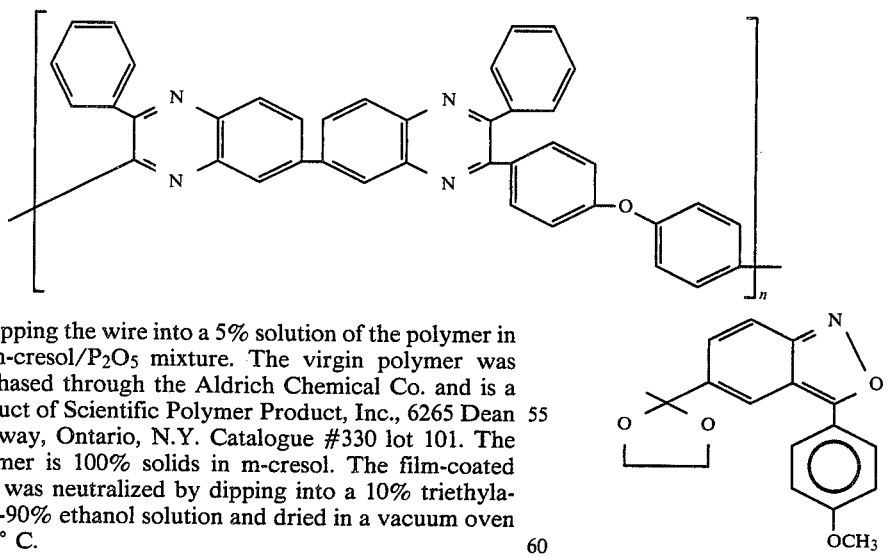

Analysis calculated for C$_{18}$H$_{17}$O$_4$N

|   | Calc. | Fnd. |
|---|---|---|
| % C | 69.44 | 68.16% |
| H | 5.50 | 5.41 |
| N | 4.50 | 4.26 |

Example 13b

Hydrogenation of the Product of Example 13a 17.12 g (0.055 mol) of the product of Example 13a was dissolved in 150 ml of tetrahydrofuran and 4 ml of triethylamine in a 500 ml 3-neck flask provided with a gas inlet tube, reflux condenser, thermometer and a magnetic stirrer. 1.2 g of 5% Pd/carbon catalyst was added.

The flask was flushed with nitrogen and then connected to a slow stream of hydrogen.

The reaction was stirred magnetically at room temperature for 9 hours.

Thin layer chromatography indicated complete reaction.

The reaction was flushed with nitrogen, and the catalyst filtered off through celite.

The filtrate was evaporated to an oily residue, 19.3 g.

The product had the formula:

Example 13c

Hydrolysis of the Product of Example 13b 19.1 g of the product of Example 13b was dissolved in 60 ml of tetrahydrofuran and 30 ml of water in a 250 ml round bottom flask. The pH of the solution was adjusted to approximately 3 with conc. HCl and the reaction allowed to stand at room temperature for approximately 18 hours.

Thin layer chromatography showed complete hydrolysis.

The reaction mixture was poured into 300 ml of saturated $Na_2CO_3$ solution and extracted three times with an equal volume of methylene chloride.

The combined methylene chloride solution was washed with water, dried and evaporated to give 14.5 g of yellow residue.

The product was recrystallized from methylenechloride hexane m.p. 119°–123° C.

The product had the formula:

Analysis calculated for $C_{16}H_{15}O_3N$

|  | Calc. | Fnd. |
|---|---|---|
| % C | 71.36 | 71.33% |
| % H | 5.61 | 5.69 |
| % N | 5.20 | 5.78 |

Example 13d

Preparation of Poly 2,6-(4-p-methoxyphenyl)quinoline

The catalyst solution was prepared by dissolving 9.44 g (66.5 mmoles) of $P_2O_5$ (weighed in a dry box) in 24 ml of m-cresol (Aldrich gold label) in a 50 ml 3-neck round bottom flask fitted with a mechanical stirrer, reflux condenser and an $N_2$ inlet.

The catalyst solution was mechanically stirred and heated in an oil bath at 105° C., under an $N_2$ blanket, until the solution became homogeneous (approximately 2½ hours). 3 g (11.16 mmoles) of the monomer of Example 13c was added followed by 10 ml of m-cresol. The temperature of the oil bath was increased to 120° and the polymerization reaction run of this temperature for 48 hours. The color of the solution changed from gold to deep red and the solution became more viscous.

The polymerization solution was poured slowly into 500 ml of a 10% solution of triethylamine in ethanol and stirred at room temperature overnight. On neutralization the polymer formed a spindle.

The polymer was collected by filtration, washed with ethanol and extracted with ethanol in a Soxhlet extractor overnight.

Following the extraction, it was filtered and dried in vacuo at 70° C. to give 2.3 g (88.5%) of dry polymer.

The polymer had the formula:

Analysis:

|  | Calc.* | Fnd. |
|---|---|---|
| % C | 82.38 | 78.52 |
| H | 4.75 | 4.40 |
| N | 6.01 | 5.52 |

[n] = .83 dl/g (measured in $H_2SO_4$).
* = based on $C_{16}H_{11}NO$

Thereafter, the polymer was rendered conductive in accordance with the procedures for Example 3 using 0.5 molar solution of sodium anthracenide in THF instead of sodium naphthalide. The conductivity was measured in accordance with Example 4. The polymer had a conductivity of 2.5 $ohm^{-1} cm^{-1}$.

Example 14

Preparation of Poly 2,6-(1-Methyl-4-phenylquinolinium)methosulfate

Poly 2,6-(4-phenylquinoline) coated platinum wires were placed in a 50 ml round bottom flask and covered with 10 ml of Dimethyl sulfate (Aldrich). The flask was fitted with a reflux condenser and a drying tube inside a hood. The reaction was allowed to stand at room temperature overnight and then heated at reflux for 6 hours.

After cooling, dimethyl sulfate solution was decanted off and the wires quenched with approximately 30 ml of a 10% solution of triethylamine in ethanol. Following neutralization the wires were thoroughly washed with ethanol and dried in vacuo at 80° C.

The polymer had the formula:

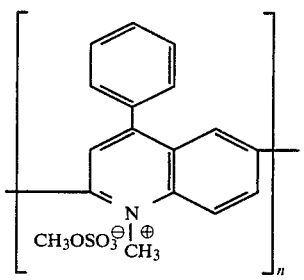

The polymer was rendered conductive in accordance with Example 3. However, the dopant was 0.5 molar sodium anthracenide in THF. The conductivity of the polymer was 0.75 ohm$^{-1}$ cm$^{-1}$ as measured in accordance with Example 4.

Example 15

Electrochemical Doping of Poly 2,6-(1-methyl-4-phenyl)quinolinium

A 5-inch platinum wire was coated with a thin film of poly 2,6-(4-phenylquinoline) as in Example 10. The polymer was then quaternized as in Example 14.

The resulting polymer coated wire was connected to the apparatus described in Example 10 and immersed into a 0.1M solution of tetraethylammonium tetrafluoroborate in acetonitrile. A linear potential sweep varying from $-0.5$ to $-1.3$ volts vs. SCE was applied to the platinum wire. The output current was essentially nil until the potential reached about $-0.8$ volts, at which point the cathodic current increased rapidly, peaking at $-1.1$ volts. Upon reversal of the potential sweep, an anodic current was observed, peaking at $-0.8$ volts.

This behavior indicates an initial resistance to current flow followed by a rapid uptake of electrons to form a reduced polymer. In effect the polymer was made electroactive by the application of a potential of about $-1.1$ volts vs. SCE in the presence of an electrolyte solution.

Example 16

Electrochemical Doping of Copolymer From 4,4'-Diamino-3,3'-dibenzoyldiphenylether and p-diacetylbenzene A 5-inch platinum wire was coated with a thin film of the polymer of Example 6d by dipping the wire into a 5% solution of the polymer in a m-cresol/P$_2$O$_5$ mixture. The film-coated wire was neutralized by dipping into a 10% triethylamine-90% ethanol solution and dried in a vacuum oven at 60° C.

The polymer coated wire was connected to the apparatus described in Example 10 and immersed into a 0.1M solution of tetraethylammonium tetrafluoroborate in acetonitrile. A linear potential sweep, varying from 0 to $-2.5$ volts vs. SCE was applied to the platinum wire. The output current was essentially nil until the potential reached about $-1.7$ volts. At that point the cathodic current increased rapidly to a maximum at $-2.2$ volts and exhibited a double wave with a peak separation of 200 mV. Upon reversal of the potential sweep an anodic current, also exhibiting a double wave, was observed at $-1.8$ volts. When the initial $-1.7$ volt potential was applied, the polymer adhering to the wire changed from a nearly colorless transparent appearance to a dark, metallic color. This color disappeared upon raising the voltage to greater than $-1.5$ volts.

This behavior indicates an initial resistance to current flow followed by a rapid uptake of electrons resulting in a charged polymer containing tetraethylammonium ion as the charge compensating ionic dopant. In effect the polymer was made electroactive by the application of a potential of about $-2.2$ volts vs. SCE in the presence of an electrolyte solution capable of providing charge compensating ionic dopants.

Example 17

Electrochemical Doping of Copolymer from 4,4'-Diamino-3,3'-dibenzoylbiphenyl and 4,4'-diacetylbiphenyl A 5-inch platinum wire was coated with a thin film of the polymer of Example 8d by dipping the wire into a 5% solution of the polymer in m-cresol/P$_2$O$_5$ mixture. The film-coated wire was neutralized by dipping into a 10% triethylamine-90% ethanol solution and dried in a vacuum oven at 60° C.

The polymer coated wire was connected to the apparatus described in Example 10 and immersed into a 0.1M solution of tetraethylammonium tetrafluoroborate in acetonitrile. A linear potential sweep, varying from 0 to $-2.5$ volts vs. SCE was applied to the platinum wire. The output current was essentially nil until the potential reached a valve of $-1.7$ volts. At that point the cathodic current increased rapidly, peaking at $-2.0$ volts. Upon reversal of the potential sweep, an anodic current was observed, peaking at $-1.6$ volts. When the initial $-1.7$-volt potential was applied, the polymer adhering to the wire turned from pale yellow to a dark, metallic color. This color disappeared upon raising the voltage to greater than $-1.4$ volts.

This behavior indicates an initial resistance to current flow followed by a rapid uptake of electrons resulting in a charged polymer containing tetraethylammonium ion as the charge compensating ionic dopant. In effect the polymer was made electroactive by the application of a potential of about $-2.0$ volts vs. SCE in the presence of an electrolyte solution capable of providing charge compensating ionic dopants.

Example 18

Electrochemical Doping of Poly 2,6-(4-(4'-chlorophenyl)quinoline)

A 5-inch platinum wire was coated with a thin film of the polymer of Example 9 by dipping the wire into a 5% solution of the polymer in a m-cresol/P$_2$O$_5$ mixture. The film-coated wire was neutralized by dipping into a 10% triethylamine-90% ethanol solution and dried in a vacuum oven at 60° C.

The polymer-coated wire was connected to the apparatus described in Example 10 and immersed into a 0.1M solution of tetrabutylammonium bromide in acetonitrile. A linear potential sweep, varying from 0 to $-2.3$ volts vs. SCE was applied to the platinum wire. The output current was essentially nil until the potential reached about $-1.5$ volts. At that point the cathodic current increased rapidly, peaking at $-1.8$ volts. Upon reversal of the potential sweep an anodic current was observed, peaking at $-1.3$ volts. When the initial $-1.5$ volt potential was applied, the polymer adhering to the wire turned to a dark metallic color. This color disappeared upon raising the voltage to greater than $-1.2$ volts.

This behavior indicates an initial resistance to current flow followed by a rapid uptake of electrons resulting in a charged polymer containing tetraethylammonium ion as the charge compensating ionic dopant. In effect the polymer was made electroactive by the application of a potential of about $-1.8$ volts vs. SCE in the presence of an electrolyte solution capable of providing charge compensating ionic dopants.

Example 19

Electrochemical Doping of Poly 2,6-(4-(4'-methoxyphenyl)quinoline)

A 5-inch platinum wire was coated with a thin film of the polymer of Example 13d by dipping the wire into a 5% solution of the polymer in a m-cresol/$P_2O_5$ mixture. The film-coated wire was neutralized by dipping into a 10% triethylamine-90% ethanol solution and dried in a vacuum oven at 60° C.

The polymer-coated wire was connected to the apparatus described in Example 10 and immersed into a 0.1M solution of tetrabutylammonium bromide in acetonitrile. A linear potential sweep, varying from 0 to $-2.3$ volts vs. SCE was applied to the platinum wire. The output current was essentially nil until the potential reached about $-1.5$ volts. At that point the cathodic current increased rapidly, peaking at $-2.1$ volts. Upon reversal of the potential sweep an anodic current was observed, peaking at $-1.5$ volts. When the initial $-1.5$ volt potential was applied, the polymer adhering to the wire turned to a dark metallic color. This color disappeared upon raising the voltage to greater than $-1.3$ volts.

This behavior indicates an initial resistance to current flow followed by a rapid uptake of electrons resulting in a charged polymer containing tetraethylammonium ion as the charge compensating ionic dopant. In effect the polymer was made electroactive by the application of a potential of about $-2.1$ volts vs. SCE in the presence of an electrolyte solution capable of providing charge compensating ionic dopants.

Example 20

Doping and Conductivity Measurement of Poly 2,6-(4-phenylquinoline)

The polymer poly 2,6-(4-phenylquinoline) was doped and rendered electroactive in accordance with Examples 3 and 4. However, the conductivity modifier was 0.5 molar sodium anthracenide in THF. The conductivity of the electroactive polymer was 20 ohm$^{-1}$ cm$^{-1}$.

Example 21

Doping and Conductivity Measurement of Poly 2,6-(4-(4'-chlorophenyl)quinoline)

The polymer of Example 9 was doped and rendered electroactive and the conductivity thereof was determined in accordance with Examples 3 and 4. However, the conductivity modifier was 0.5 molar sodium anthracenide in THF. The conductivity of the electroactive polymer was 1.25 ohm$^{-1}$ cm$^{-1}$.

Example 22

Doping and Conductivity Measurement of Poly 2,6-(4-phenylquinoline)

The polymer poly 2,6-(4-phenylquinoline) was doped and rendered electroactive and the conductivity thereof was determined in accordance with Examples 3 and 4. However, the conductivity modifier was 0.1 molar sodium anthracenide in THF. The conductivity of the electroactive polymer was 15 ohm$^{-1}$ cm$^{-1}$.

Example 23

Doping and Conductivity Measurement of Poly 2,6-(4-phenylquinoline)

The polymer poly 2,6-(4-phenylquinoline) was doped and rendered electroactive and the conductivity thereof was determined in accordance with Examples 3 and 4. However, the conductivity modifier was 0.01 molar sodium anthracenide in THF. The conductivity of the electroactive polymer was 15 ohm$^{-1}$ cm$^{-1}$.

Example 24

Doping and Conductivity Measurement of Poly 2,6-(4-phenylquinoline)

The polymer poly 2,6-(4-phenylquinoline) was doped and rendered electroactive and the conductivity thereof was determined in accordance with Examples 3 and 4. However, the conductivity modifier was 0.005 molar sodium anthracenide in THF. The conductivity of the electroactive polymer was 2.75 ohm$^{-1}$ cm$^{-1}$.

Example 25

Casting of Free-Standing Films of Poly-Phenylquinoxaline

Poly 2,2'-(p,p'oxidiphenylene)-6,6'-Bi(3-phenylquinoxaline) was purchased from Scientific Polymer Products (6265 Dean Parkway, Ontarion, N.Y., 14519. Catalog #330 Lot #01). The polymer was dissolved in m-cresol. Free-standing films were cast using the procedure described in Example 2, except that neutralization occurred either in methanol or water.

Example 26

Electrochemical Synthesis of Tetraethyl Ammonium Anthracenide Dopant

To 100 ml of 0.1M $Et_4N^+BF_4^-$ in dry acetonitrite was added 0.0025 mole of anthracene. The solution/suspension was placed in a 200-ml beaker in the inert atmosphere dry box and fitted with a mechanical stirrer, Pt gauze working electrode, Ag/AgNO$_3$ reference electrode, and a Pt foil counter electrode (isolated by a porous Vycor tube). The working electrode was held at $-2.5$ V vs. Ag/AgNO$_3$ during 1 hour while the solution was stirred. The current passed ranged from 30–40 mA. The resulting dark blue solution was used immediately.

Example 27

Chemical Doping of Polyphenylquinoxaline Free-Standing Films

Free-standing films as described in Example 25 were immersed in high purity grade acetonitrile for 24 hours in an inert atmosphere dry box. The soaked films were placed directly into an electrochemical cell which was producing the dopant solution described in Example 26. The films were allowed to contact the dopant for a period of 11 minutes. Upon contact with the dopant solution, the films changed their color from their original brown to a deep blue-black with metallic luster. The doped films were removed from the doping cell, washed with fresh acetonitrile and allowed to dry. The conductivity of the doped films was measured with a four-point probe using the procedures described in Example 4. A conductivity value of $3 \times 10^{-4}$ ohm$^{-1}$cm$^{-1}$ was measured.

Example 28

Preparation and Doping of Poly-2,2'-(p-phenylene)-6,6'-(3-phenylquinoxaline)

This polymer was prepared according to the route by Hergenrother and Levine, J. Polymer Sci., A-1, Vol. 5, 1453 (1967). The monomers, 3,3'-diaminobenzidine and 1,4-bisphenylglyoxylbenzene, were purchased from Aldrich and ICN, respectively. Both were purified by recrystallization prior to use. A 25-ml, three-neck flask equipped with a mechanical stirrer, reflux condenser, and argon inlet was charged with 0.2143 g (1 mmole) of 3,3'-diaminobenzidine, 0.3422 g (1 mmole) of 1,4-bisphenylglyoxylbenzene, and 25 ml of m-cresol. The flask containing the reactants under argon was slowly heated over a two-hour period to 120° C. This temperature was maintained for an additional hour, after which the reaction mixture became very viscous. The reaction was terminated by quneching with methanol, resulting in the precipitation of the polymer. After filtering and further washing with fresh methanol, the polymer was Soxhlet-extracted with methanol for 24 hours and dried overnight in a vacuum oven at 60° C. The yield for the reaction was 79% (0.384 g of polymer). The polymer was readily soluble in ordinary organic solvents, such as chloroform, from which free-standing films were cast. This polymer has the following structure:

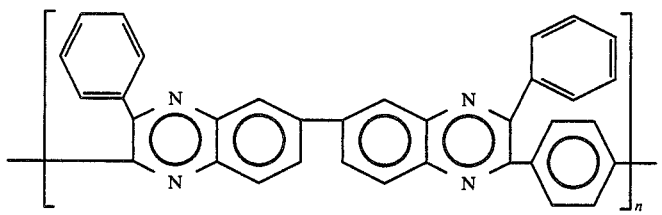

Electrochemical screening via cyclic voltammetry (CV) showed two reversible reduction waves at $-1.9$ and $-2.1$ volt. Electrochemically doped films registered a room temperature, four-point probe conductivity of $5 \times 10^{-2}$ S/cm.

What is claimed is:

1. An electroactive polymer which comprises a charged polymer backbone of recurring diradical units of a fused 6,6 membered nitrogen-containing unsaturated heterocyclic ring system and charge compensating ionic dopants associated therewith wherein the polymer backbone is capable of undergoing a reversible oxidation or a reversible reduction or both to form said charged polymer backbone and said heterocyclic ring system contains at least two nitrogen atoms and none of said nitrogen atoms occupy the ring fusion position.

2. The electroactive polymer according to claim 1 wherein the diradicals have from two to six nitrogen atoms distributed within and among the fused six-member rings wherein no more than two nitrogens are bonded sequentially within said ring system.

3. The electroactive polymer according to claim 2 wherein the fused rings contain two nitrogens and are positional diradicals of cinnoline; quinazoline; quinoxaline; 2-phenyl-quinoxaline; phthalazine; 1,5-naphthyridine; 1,6-naphthyridine; 1,7-naphthyridine; 1,8-naphthyridine; 2,6-naphthyridine; and copyrine.

4. The electroactive polymer according to claim 2 wherein the fused rings contain three nitrogens and are positional diradicals of 1,2,4-benzotriazine; pyrido[3,2-d]pyrimidine; pyrido[4,3-d]pyrimidine; pyrido[3,4-d]pyrimidine; pyrido[2,3-d]pyrimidine; pyrido[2,3-b]pyrazine; pyrido[3,4-b]pyrazine; pyrido[2,3d]pyridazine; and pyrido[3,4-d]pyridazine.

5. The electroactive polymer according to claim 2 wherein the fused rings contain four nitrogens and are positional diradicals of pyridazino[4,5-c]pyridazine; pyrimido[5,4-d]pyrimidine; pteridine; pyrimido[4,5-d]pyridazine; pyrimido[4,5-d]pyrimidine; pyrazino[2,3-b]pyrazine; pyrazino[2,3-d]pyridazine; pyridazino[4,5-d]pyridazine; pyrimido[4,5-c]pyridazine; pyrazino[2,3-c]pyridazine; pyrido[3,2-d]-as-triazine; and pyrido[2,3-e]-as-triazine.

6. The electroactive polymer according to claim 2 wherein the fused rings contain five nitrogens and are positional diradicals of pyrimido[4,5-e]-as-triazine and pyrimido[5,4-d]-as-triazine.

7. The electroactive polymer according to claim 2 wherein the fused rings contain six nitrogens and are positioned diradicals of as-triazino[6,5-d]-as-triazine.

8. The electroactive polymer according to claim 2 wherein the recurring units are positional diradicals of quinoxaline, substituted quinoxaline derivatives, or mixtures thereof, wherein said substituted quinoxaline derivatives contain one substituent on the nitrogen containing portion of the ring and one or two substituents on the carbocyclic portion of the ring, said substituents independently selected from H; amino; alkyl of 1 to 4 carbon atoms; alkoxy of 1 to 4 carbon atoms; an alkylthio of 1 to 4 carbon atoms; a cycloaliphatic group of 5 or 6 carbon atoms; an alkenyl grup of 2 to 4 carbon atoms; an aryl group of 6 to 10 carbon atoms; an aryl group of 6 to 10 carbon atoms substituted by 1 to 3 alkyl groups of 1 to 4 carbon atoms, alkenyul groups of 1 to 4 carbon atoms, alkynyl groups of 1 to 4 carbon atoms, alkoxy groups of 1 to 4 carbon atoms, 1 to 3 cyano groups, 1 to 3 halogen atoms, dialkyl amino groups of 1 to 4 carbon atoms, an alkylthio of 1 to 4 carbon atoms; and a 5- or 6-membered nitrogen-containing unsaturated heterocyclic group.

9. The electroactive polymer according to claim 8 wherein the charge compensating dopant is a cation.

10. The electroactive polymer according to claim 9 wherein said quinoxaline and substituted quinoxaline recurring units are diradicals connected at the 2,6 and 3,6 positions, and mixtures of said diradicals.

11. The electroactive polymer according to claim 2 wherein the recurring units are selected from the group consisting of quinoxaline diradicals, substituted quinoxaline diradicals or mixtures thereof, wherein the diradicals are interspersed by a connecting unit and the diradicals are connected through positions selected from the group consisting of the 2,6 or 3,6 positions and mixtures said positions thereof, wherein the connecting unit is selected from the group consisting of:

—O—; —S—; —CH=CH—; —C≡C—;

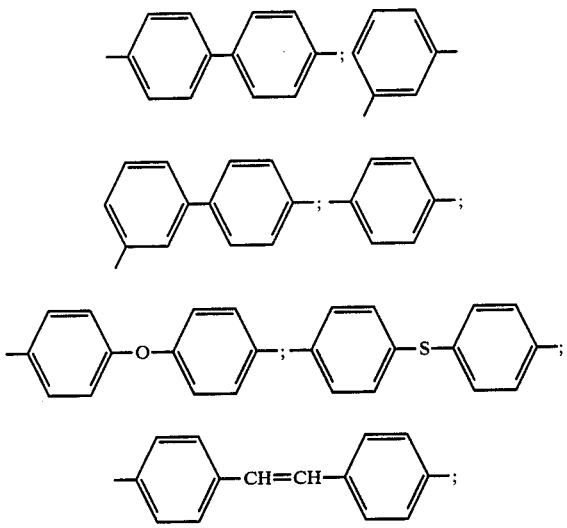

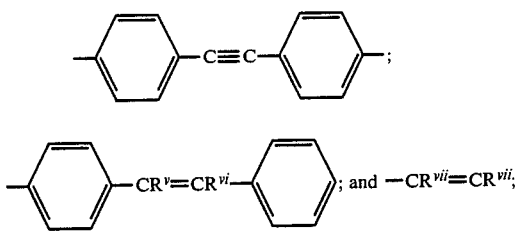

wherein $R^v$, $R^{vi}$, and $R^{vii}$ are H or methyl; and mixtures of said connecting units.

12. The electroactive polymer according to claim 11 wherein the substituted quinoxaline recurring units are diradicals connected at the 2,6 positions and the substituent is at the three position.

13. The electroactive polymer according to claim 12 wherein the connecting unit is selected from the group consisting of p-phenylene, m-phenylene, p,p' oxidiphenylene and mixtures thereof.

14. The electroactive polymer according to claim 13 wherein the substituent is a phenyl group.

15. The electroactive polymer according to claim 3 wherein the recurring units are quinoxaline diradicals connected at the 2,6 and 3,6 positions and mixtures thereof.

16. The electroactive polymer according to claim 11 wherein charge compensating ionic dopant is a cation selected from the group consisting of the alkali metal ions, alkali earth metal ions, Group III metal ions,

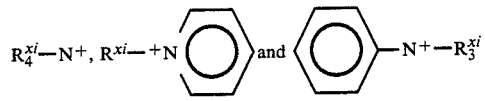

wherein $R^{xi}$ is a straight or branched chain alkyl of $C_1$-$C_6$ groups or mixtures of said cations.

17. The electroactive polymer according to claim 16 wherein the recurring unit has the formula:

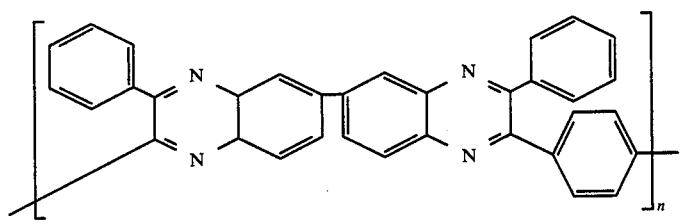

18. The electroactive polymer according to claim 16 wherein the recurring unit has the formula:

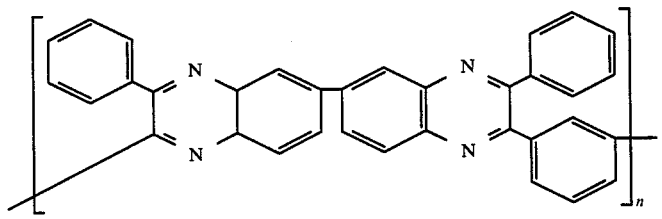

19. The electroactive polymer according to claim 16 wherein the recurring unit has the formula:

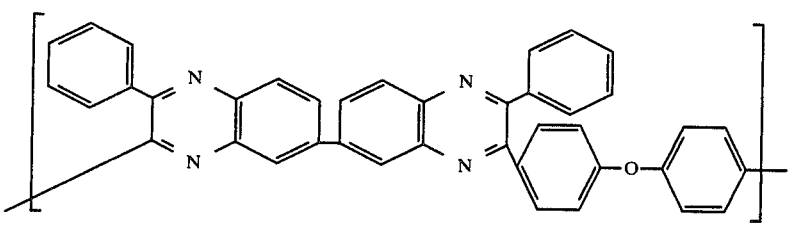

20. An electroactive polymer which comprises a charged polymer backbone and charge compensating ionic dopants associated therewith of the formula:

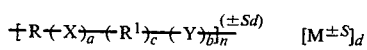

wherein a is 0 or 1; b is 0 or 1; c is 0 or 1; n is an integer from 2 to 2,000; d is an integer from 1 to 40,000; s is an integer 1, 2, or 3; R is a fused six-member nitrogen-containing unsaturated diradical-heterocyclic ring system; $R^1$ is the same as R or a different fused six-member unsaturated heterocyclic ring system; X is a connecting unit; Y is the same connecting unit as X or a different connecting unit; and M is a charge compensating ionic dopant of opposite electrical charge to the charge of the polymer backbone wherein the polymer backbone is capable of undergoing reversible oxidation or reversible reduction or both to form said charged polymer backbone.

21. The electroactive polymer according to claim 20 wherein R and R' contain from two to six nitrogen atoms distributed within and among the fused six-member rings wherein each ring contains two or fewer nitrogens bonded sequentially and none of said nitrogens occupy ring fusion positions.

22. The electroactive polymer according to claim 21 wherein the R and R' are substituted quinoxaline.

23. The electroactive polymer according to claim 21 wherein R and $R^1$ are quinoxaline, substituted quinoxaline or mixtures thereof.

24. The electroactive polymer according to claim 23 wherein R and R' is quinoxaline, substituted quinoxaline and mixtures thereof, X and Y connect R and $R^1$ at the 2,6.

25. The electroactive polymer according to claim 24 wherein R and R' are 2,6-quinoxaline with the formula

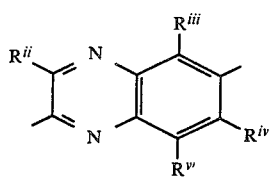

$R^{ii}$, $R^{iii}$, $R^{iv}$ and $R^{v}$ are a substituent groups selected from H; amino; alkyl 1 to 4 carbon atoms; alkoxy 1 to 4 carbon atoms; an alkylthio of 1 to 4 carbon atoms; a cycloaliphatic group of 5 or 6 carbon atoms; an alkenyl group of 2 to 4 carbon atoms; an aryl group of 6 to 10 carbon atoms; an aryl group of 6 to 10 carbon atoms substituted by 1 to 3 alkyl groups of 1 to 4 carbon atoms, alkenyl groups of 1 to 4 carbon atoms, alkynyl groups of 1 to 4 carbon atoms, alkoxy groups of 1 to 4 carbon atoms, 1 to 3 cyano groups, 1 to 3 halogen atoms, dialkyl amino groups of 1 to 4 carbon atoms, an alkylthiol of 1 to 4 carbon atoms; a 5- or 6-member nitrogen containing unsaturated heterocyclic group.

26. The electroactive polymer according to claim 25 wherein $R^{iii}$, $R^{iv}$ and $R^{v}$ are H.

27. The electroactive polymer according to claim 25, wherein the connecting unit X and Y are selected from the group consisting of

—O—; —S—; —CH=CH—; —C≡C—;

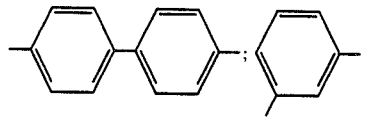

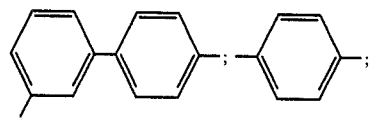

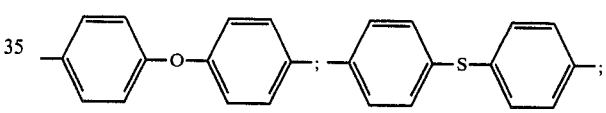

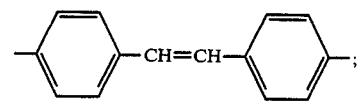

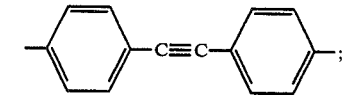

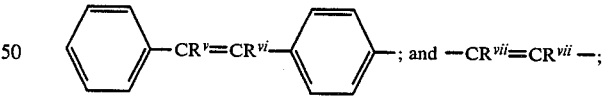

wherein $R^v$, $R^{vi}$, and $R^{vii}$ are H or methyl; and mixtures of said connecting units.

28. The electroactive polymer according to claim 27 wheren a, b and/or c are zero and n is from 10 to 20,000.

29. The electroactive polymer according to claim 28 wherein the molecular weight is equal to or greater than about 10,000.

30. The electroactive active polymer according to claim 29 wherein a is 1, b and c are zero and the recurring unit has the formula:

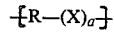

31. The electroactive polymer according to claim 30 wherein a, b and c are zero and the recurring unit has the formula:

−(R)−

32. The electroactive polymer according to claim 29 wherein the charge compensating ionic dopant is a cation selected from the group consisting of the alkali metal ions, alkali earth metal ions, Group III metal ions, and

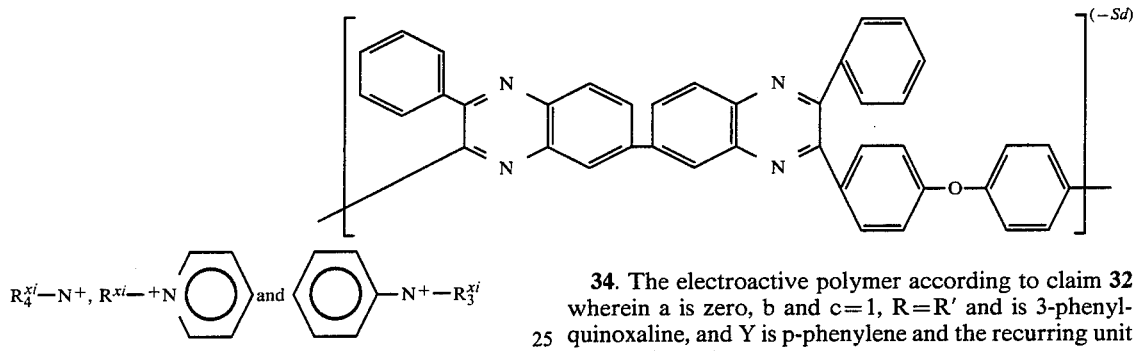

wherein $R^{xi}$ is a straight or branched chain alkyl of $C_1-C_6$ groups, or mixtures of said cations.

33. The electroactive polymer according to claim 32 wherein a is zero and b and c=1, $R=R^1$ and is phenylquinoxaline, and Y is

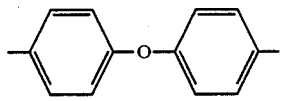

and the recurring unit has the formula:

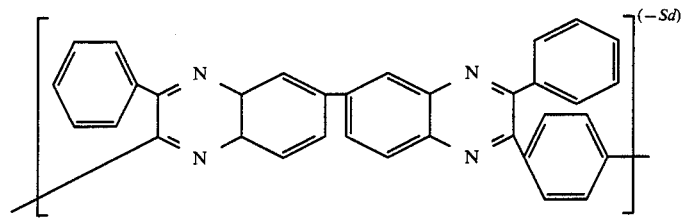

34. The electroactive polymer according to claim 32 wherein a is zero, b and c=1, $R=R'$ and is 3-phenylquinoxaline, and Y is p-phenylene and the recurring unit has the formula:

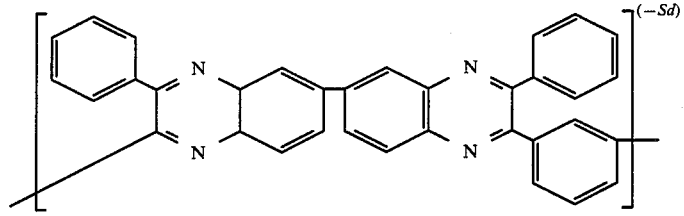

35. The electroactive polymer according to claim 32 wherein a is zero, b and c=1, $R=R'$ and is 3-phenylquinoxaline, and Y is m-phenylene and the recurring unit has the formula:

* * * * *